United States Patent [19]

Oprandy

[11] Patent Number: 5,679,519
[45] Date of Patent: Oct. 21, 1997

[54] MULTI-LABEL COMPLEX FOR ENHANCED SENSITIVITY IN ELECTROCHEMILUMINESCENCE ASSAY

[76] Inventor: John J. Oprandy, 17914 Hickman St., Poolesville, Md. 20837

[21] Appl. No.: 437,348

[22] Filed: May 9, 1995

[51] Int. Cl.$^6$ .............................. C12Q 1/68; C12Q 1/70; C12P 19/34; C07H 21/04
[52] U.S. Cl. .................................. 435/6; 435/5; 435/91.2; 435/7.1; 435/7.9; 536/26.6; 536/24.3; 536/24.32; 536/24.33; 252/515
[58] Field of Search ................................ 435/6, 5, 91.2, 435/7.1, 7.9; 536/26.6, 24.3, 24.33, 24.32; 252/515

[56] References Cited

U.S. PATENT DOCUMENTS

| | | |
|---|---|---|
| 4,372,745 | 2/1983 | Mandle et al. . |
| 4,925,785 | 5/1990 | Wang et al. . |
| 5,108,893 | 4/1992 | Baret et al. ................................ 435/6 |
| 5,124,246 | 6/1992 | Urdea et al. . |
| 5,175,270 | 12/1992 | Nilsen et al. . |
| 5,180,828 | 1/1993 | Ghazarossian et al. .................. 546/37 |
| 5,235,808 | 8/1993 | Taylor . |
| 5,310,687 | 5/1994 | Bard et al. . |
| 5,433,896 | 7/1995 | Kang et al. ............................. 252/700 |

OTHER PUBLICATIONS

Black burn et al. "Electrochemiluminescence Detection for Development of Immunoassays and DNA Probe Assays for Clinical Diagnostics," Clinical Chemistry, vol. 37/No. 9:1534-1539 (1991). Only one page provided, BR obtained.

Leland and Powel, "Electrogenerated Chemiluminescence: An Oxidative-Reduction Type ECL Reaction Sequence Using Tripropyl Amine," J. of the Electrochemical Society, vol. 137: 3127-3129 (1990).

Yang et al. "Electrochemiluminescence: A New Diagnostic and Research Tool," Bio/Technology, vol. 12 193-194 (1994).

Primary Examiner—W. Gary Jones
Assistant Examiner—Dianne Rees
Attorney, Agent, or Firm—John W. Ryan; Patrick J. Igoe; John L. Lemanowicz

[57] ABSTRACT

A nucleotide probe complex which enhances the ability to discriminate low level samples in electrochemiluminescent assays. The complex is composed of a platform molecule to which multiple copies of an organometallic electrochemiluminescent label and an oligonucleotide probe are separately attached. Preferably the complex is capped with streptavidin. Use of the complex permits detection of 1000 copies of analyte per sample in less than one hour.

20 Claims, 13 Drawing Sheets

MULTI-LABEL COMPLEX FOR ENHANCED SENSITIVITY IN ELECTROCHEMILUMINESCENCE ASSAY

FIELD OF THE INVENTION

The present invention relates to certain improvements in nucleic acid assays involving electrochemiluminescence (ECL) and complexes suitable for use therein.

BACKGROUND OF THE INVENTION

Nucleic acid hybridizations are commonly used in genetic research, biochemical research and clinical diagnostics. In basic nucleic acid hybridization assays, single stranded nucleic acid (either DNA or RNA) is hybridized to a labeled nucleic acid probe and the resulting duplex is detected.

Diagnostic assays based on hybridization frequently require amplification of the nucleic acid in the sample under test. Usually a polymerase chain reaction (PCR) is used for such amplification. However, many clinical laboratories and most doctors' offices are resistant to PCR because of its complexity and the possibility of amplifying contaminants. Assays which do not require amplification are more popular because, generally speaking, they are less labor intensive and take a shorter period of time to perform. There is, however, a growing need for non-amplified assays which have improved sensitivity and accuracy.

There are essentially three methods for improving sensitivity in non-amplified DNA probe assays: (1) primer extension, (2) extended incubation time and (3) multi-label macromolecular complexes. Some prior efforts to provide assays which do not require amplification are those shown in U.S. Pat. Nos. 5,175,270, 5,124,246, 4,925,785 and 4,372,745.

U.S. Pat. No. 5,175,270 discloses the use of multi-layered DNA constructs in the context of nucleic acid hybridization assays to reduce background noise and to initially enhance signal strength for very low copy sequences at short exposure times (overnight v. 2–6 weeks). The outermost layer of a given DNA matrix has single stranded sequences exposed to the surface which hybridize with a predetermined nucleic acid sequence. The assay formats specifically mentioned are Southern blotting hybridizations or dot hybridizations although others also are envisioned.

U.S. Pat. No. 5,124,246 discloses a scheme for binding multiple labelled probes onto a given target DNA employing branched DNA in a multi-layered oligo probe complex. This provides multiple binding sites for a specific set of single label oligo probes.

U.S. Pat. No. 4,925,785 discloses, in the context of a nucleic acid hybridization assay, employing multiple fluorescent labels on very large random coiled polymer support material to which oligonucleotide probes are attached to amplify signal. Covalent linkages are used to attach the labels and the probes to the polymer. Hetero- and homogeneous assay formats are disclosed.

U.S. Pat. No. 4,372,745 discloses the use of encapsulated fluorescent materials as part of a signal enhancing system in the context of immunologically based assays. The multiple labels are released as part of the detection step. A variety of assay formats are taught.

Assays based on ECL are well known in the art and are finding expanding applications because of their accuracy, ease of use and freedom from radioactive materials.

A particularly useful ECL system is described in a paper by Yang et al, *Bio/Technology*, 12:193–194 (Feb. 1994). See also a paper by Massey, *Biomedical Products*, Oct. 1992 as well as U.S. Pat. Nos. 5,235,808 and 5,310,687, the contents of these papers and patents being incorporated herein by reference.

ECL processes have been demonstrated for many different molecules by several different mechanisms. In Blackburn et al (1991) *Clin. Chem.* Vol.37, No. 9, pp. 1534–1539, the authors used the ECL reaction of ruthenium (II) tris (bipyridyl), $Ru(bpy)_3^{2+}$, with tripropylamine (TPA) Leland et al (1990) *J. Electrochem. Soc.* Vol. 137, pp. 3127–31) to demonstrate the technique. Salts of $Ru(bpy)_3^{2+}$ are very stable, water-soluble compounds that can be chemically modified with reactive groups on one of the bipyridyl ligands to form activated species with which proteins, haptens, and nucleic acids are readily labeled. The activated form of the $Ru(bpy)_3^{2+}$ used by Blackburn et al was $Ru(bpy)_3^{2+}$-NHS ester:

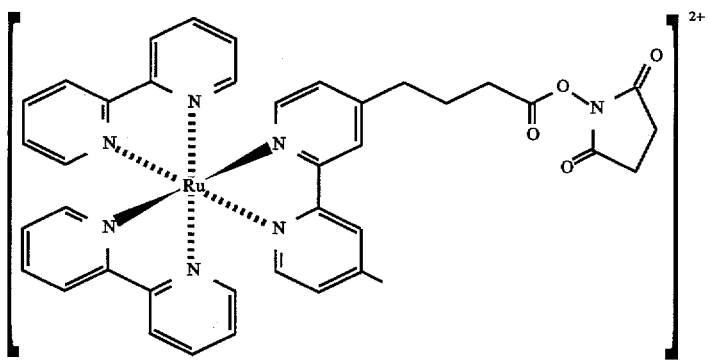

FIG. 1 shows the proposed mechanism for the ECL reaction of $Ru(bpy)_3^{2+}$ and TPA. $Ru(bpy)_3^{2+}$, the label, is oxidized at the surface of an electrode, forming the strong oxidant, $Ru(bpy)_3^{3+}$ Simultaneously, TPA which is present in large molar excess in the solution, is oxidized at the electrode to form the cation radical TPA$^+$, which rapidly and spontaneously loses a proton to form the radical TPA. $Ru(bpy)_3^{3+}$, a strong oxidant and TPA, a strong reductant, react to form the excited state of the ruthenium complex, $Ru(bpy)_3^{2+*}$, as well as other inactive products. The energy necessary for formation of the excited state arises from the large difference in electrochemical potentials of the Ru(bpy)$_3^{3+}$ and the TPA. The excited-state $Ru(bpy)_3^{2+*}$ decays through a normal fluorescence mechanism, emitting a photon at 620 nm. This process regenerates the original form of the $Ru(bpy)_3^{2+}$, which is free to cycle multiple times through the reaction sequence. Each ECL-active label, therefore, can emit many photons during each measurement cycle, thereby enhancing the detection of the label.

Quantification of the $Ru(bpy)_3^{2+}$ label can be readily automated with relatively uncomplicated instrumentation. FIG. 2 is a diagram of the essential components of instruments under development for automated immunoassays and DNA probe assays. The heart of the instrument is the electrochemical flow-cell, containing the working electrodes and counter electrodes for initiation of the ECL reaction. Both of the electrodes are fabricated from gold, but other materials have been used with various degrees of success. A potentiostat (not shown) applies various voltage waveforms to the electrodes, and a single photomultiplier tube (PMT) detects the light emitted during the ECL reaction. An Ag/AgCl reference electrode is placed in the fluid path downstream from the flow cell, and a peristaltic pump is used to draw various fluids through the flow cell. In a typical sequence, the assay fluid is drawn from a test tube into the flow cell and the label is quantified by applying a ramp voltage to the electrodes and measuring the emitted light. After the measurement, a high-pH cleaning solution is drawn into the cell for an electrochemical cleaning procedure. A conditioning solution is then drawn into the cell, and a voltage waveform is applied that leaves the surfaces of the electrodes in a highly reproducible state, ready for the next measurement cycle.

The ECL reaction can be efficiently initiated by many different voltage waveforms. FIG. 3 illustrates measurements of the working electrode current and the ECL intensity induced by the application of a triangle wave to the electrodes. The applied voltage as shown is actually the voltage measured at the Ag/AgCl reference electrode and includes the effects of a significant uncompensated resistance; consequently, the actual voltage applied at the working electrode is substantially less than that depicted. The triangle waveform rises from 565 to 2800 mV at a rate of 750 mV/s and then decreases at the same rate to 1000 mV. The current that flows in the cell is primarily the result of the oxidation of the TPA and the hydrolysis of water. Oxidation of both the TPA and $Ru(bpy)_3^{2+}$ becomes evident when the applied voltage reaches ~1100 mV and produces a luminescence. The intensity of the luminescence increases with the applied voltage until the TPA at the surface of the electrode is depleted, resulting in decreased intensity. The intensity of the observed luminescence is great enough that it can easily be measured with conventional PMTs operating either in photon-counting or current modes.

The system also includes magnetic beads suitably coated to capture the molecules of interest and bring them to the electrode surface. For this purpose, a magnet is positioned under the electrode to bring the magnetic beads coated with the target molecules.

In a conventional immunoassay using the ECL system, anti-target antibodies may be bound to the magnetic beads. Additionally, anti-target antibodies which recognize a different epitope or part of the target are combined with an ECL label to form what may be termed "reporter" or "detector" molecules. By incubating the target molecule with the magnetic beads and the labeled anti-target antibodies, a "sandwich" is formed by virtue of the attachment of the two separate antibodies to the target (antigen) at different sites. This sandwich is then drawn into the flow cell and mixed with buffer solution containing a precursor. An applied magnetic force captures the magnetic beads on the electrode surface thus stabilizing the target molecule and its attached labeled reporter for maximum detection by PMT. Unbound reagents from the sample mix are washed away by continued flow of buffer solution.

After the sample is captured, the ECL measurement is performed by application of electrical potential to the working electrode. This gives a clean signal-to-noise ratio in that only those labels which are bound to the "sandwich" that are surrounded by the precursor and in contact with the electrode emit light. Relatively little interference results from background presented by the buffer or otherwise.

The ECL system may also be used for nucleic acid hybridization-based assays with oligonucleotides being used for hybridization in lieu of the antibodies referred to above. However, for this purpose, the conventional practice has been to amplify the nucleic acids by using polymerase chain reaction (PCR) or nucleic-acid sequence-based amplification (NASBA). While the ECL process, using amplification is effective, there is a need to be able to effectively carry out the ECL assay without amplification for reasons noted earlier. The sensitivity of non-amplified nucleic acid assays to date has been between $10^3$–$10^6$ copies of DNA (data not shown). Accordingly, the principal object of the present invention is to provide such an ECL assay. Other objects will also be apparent from the description of the invention which follows.

SUMMARY OF THE INVENTION

Broadly stated, the invention contemplates the provision of a multi-labeled probe complex suitable for use in an ECL assay comprising a platform molecule carrying a plurality of electrochemiluminescent labels and may have oligonucleotide probe(s). This complex is used in combination with magnetic beads which also carry or cooperate with a hybridization probe to capture the target nucleic acid.

The concept of increasing the number of signal producing molecules associated with a probe to increase signal has previously been disclosed, notably for situations where the probes are based on the use of antibodies. This approach has limited utility, however, particularly because of possible background complications generated by the increased number of signal producing molecules. This is a particular problem where oligonucleotide probes are involved. For example, there is generally little physical space available to position multiple labels in operative association with an oligonucleotide probe without raising other complications, e.g. background noise due to non-specific binding or an overall reduction in the signal-to-noise ratio by quenching (due to close proximity of ECL labels) and also steric hinderance of specific binding.

The multi-labeled probe complex of the invention has been found to be uniquely suitable for use in an ECL assay. Central to its many advantages, the invention provides a substantially increased signal with a concomitant reduction in background. The lowering of background is due to a reduction in non-specific binding of compounds to the labeled probe complex. This process dramatically increases signal-to-noise in assays and thereby profoundly enhances the sensitivity of these assays. In addition, the invention may be practiced in such a way as to reduce the number of assay steps and also the length of time involved to complete the assay. This is a departure from the traditional approach to enhancing sensitivity in DNA probe assays by including protracted incubation times.

BRIEF DESCRIPTION OF THE DRAWINGS

FIG. 4 is a schematic of one way of practicing the invention (identified herein as Format 1) while

DESCRIPTION OF PREFERRED EMBODIMENTS

Figure 1:
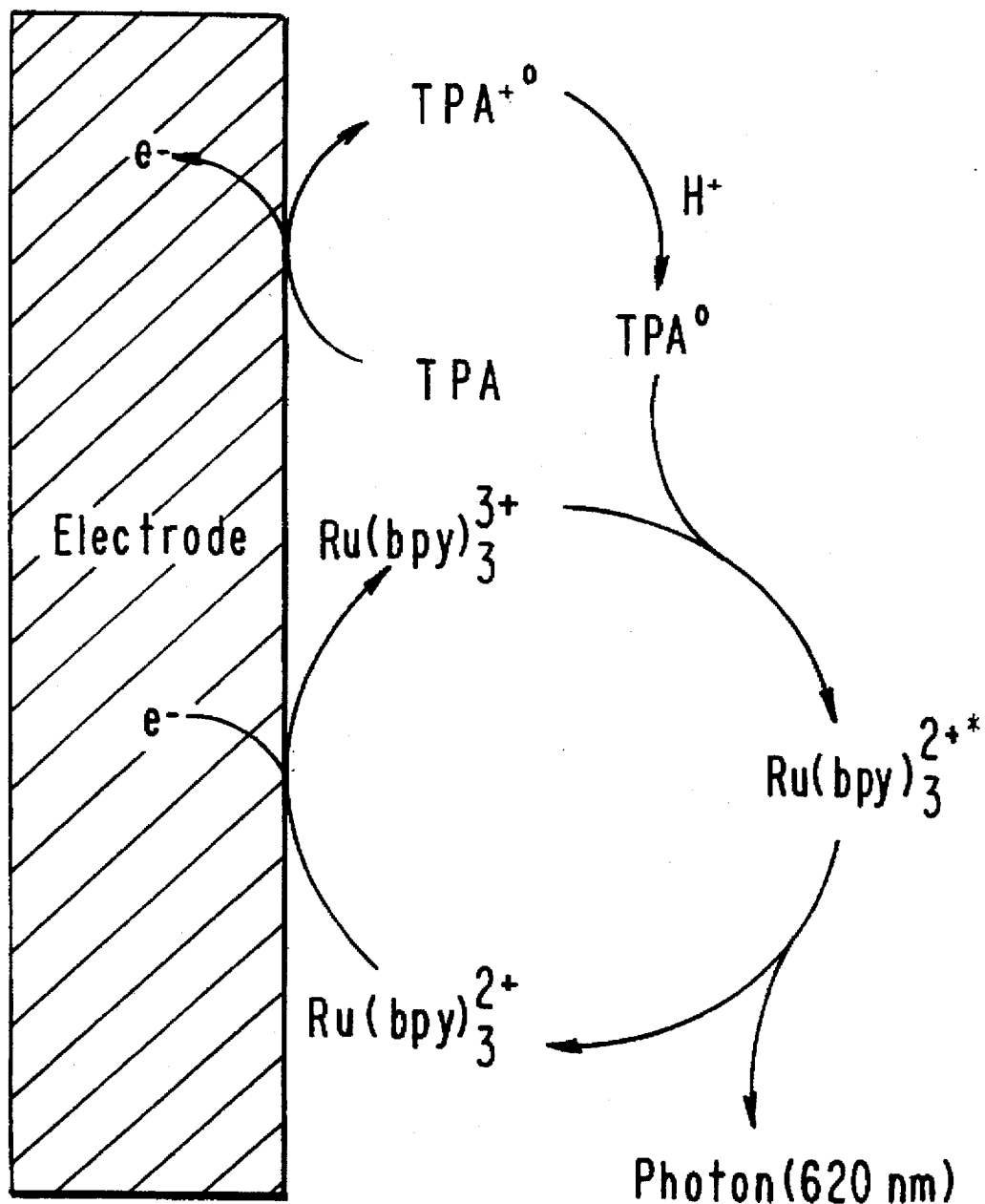
FIG. 1 Mechanism of ECL excitation. $Ru(bpy)_3^{2+}$ and TPA are oxidized at the surface of a gold or platinum electrode, forming Ru(bpy)$_3^{3+}$ and TPA$^+$, respectively. The TPA$^+$ spontaneously loses a proton, forming TPA. The TPA, a strong reductant, reacts with Ru(bpy)$_3^{3+}$, a strong oxidant, forming the excited state of the label, Ru(bpy)$_3^{2+*}$. The excited state decays to the ground state through a normal fluorescence mechanism, emitting a photon having a wavelength of 620 nm.
Figure 2:
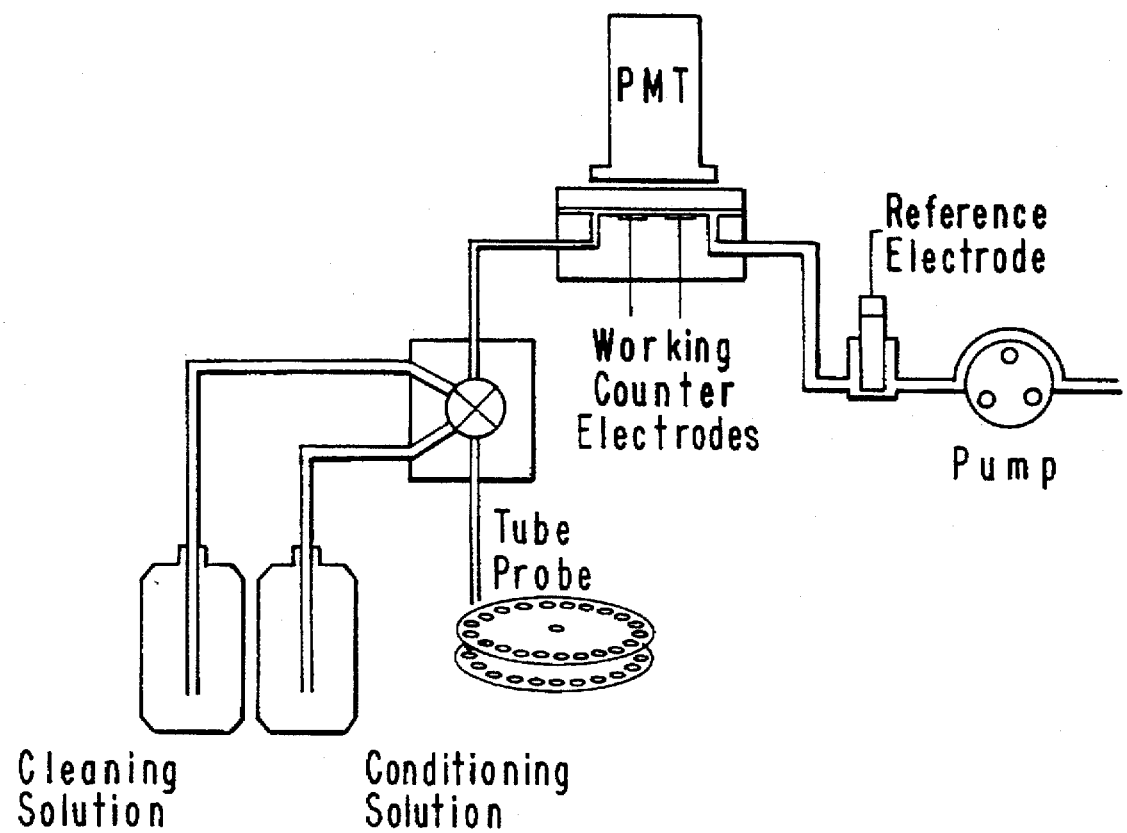
FIG. 2 Principal components of the ECL analyzer.
Figure 3:
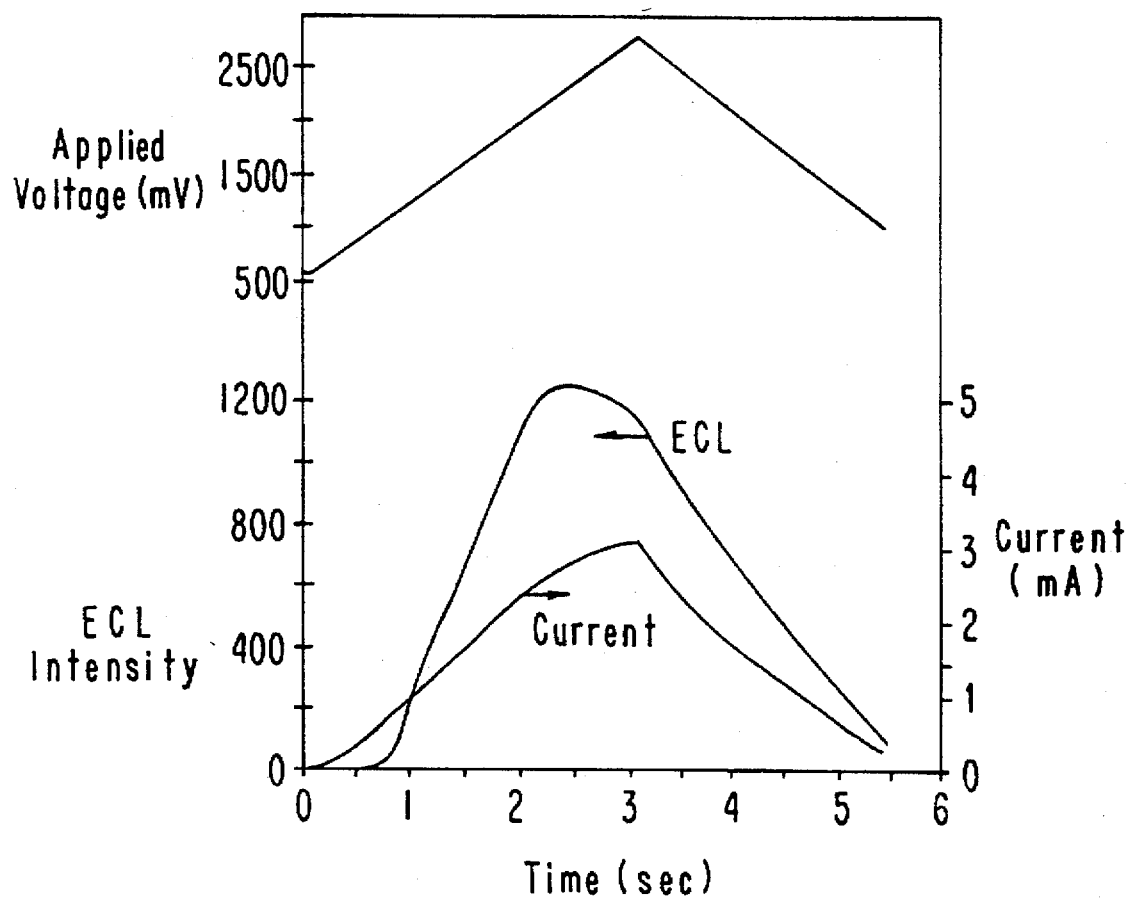
FIG. 3 Electrochemical excitation waveforms and the resulting current and luminescence waveforms. The potential is applied to the counterelectrode and the waveform shown is measured at the Ag/AgCl reference electrode. The current is measured at the working electrode, and the analytical signal (luminescence) is measured with the PMT mounted adjacent to the flow cell, as shown in FIG. 2.

The multi-labeled platform complex of the invention may take a variety of forms and may be prepared in any convenient fashion. The platform may be a synthetic or natural polymer, carbon fibrils, polystyrene beads or the like. The platform should contain, or be capable of having introduced onto it, functionalities which permit controlled addition of the label and the oligonucleotide probe or a member of an immunological pair (e.g., biotin, streptavidin, etc.) to which the probe is bound.

Bovine serum albumin (BSA) is a particularly preferred platform, especially biotinylated BSA which is commercially available with approximately 11 biotins (bio) on the molecule. The biotins provide a useful predetermined location for attachment of the labels and the oligonucleotide probe via avidin-biotin connection. Other materials equivalent to BSA may also be used as the platform.

Any oligonucleotide probe appropriate for hybridization to the target DNA or RNA may be used. Such probes can be prepared in conventional manner as known in the art. Typical oligonucleotides include sequences complementary to, for example, the sequences of such targets as HIV1 gag gene, cystic fibrosis sequence. See for example International Application No. PCT/US92/09943 and U.S. application Ser. No. 792,602 filed Nov. 15, 1991, both these documents are expressly incorporated herein by reference. The complementary sequences suitable for use in the assays include but are not limited to the following:

5'-GGT AGC TGA ATT TGT TAC TTG GCT CAT TGT CCC TGA CAT GCT GTC ATC ATT TCT TCT A-3' (SEQ ID NO:1:)

5'-TA GAA GAA ATG ATG ACA GCA TGT CAG GGA-3' (SEQ ID NO:2:)

5'-CA ATG AGC CAA GTA ACA AAT TCA GCT ACC-3' (SEQ ID NO:3:)

5-'CGA CTG TCA TCT ATC TAC ACT GTC TGC AGC TTC CTC ATT GAT GGT CTC TTT TAA CA-3' (SEQ ID NO:4:)

5'-CAT GCA CTG GAT GCA CTC TAT CCC ATT CTG CAG CTT CTT CAT TGA TGG TCT CTT TTA ACA -3' (SEQ ID NO: 5:)

5'-TG TTA AAA GAG ACC ATC AAT GAG GA-3' (SEQ ID: NO:6:)

5'-GA ATG GGA TAG AGT GCA TCC AGT GCA TG-3' (SEQ ID NO:7:)

5'- GA CAG TGT AGA TAG ATG ACA GTC G-3' (SEQ ID NO:8:)

5'-TG TTA AAA GAG ACC ATC AAT GAG GA-3' (SEQ ID NO:9:)

5'-GA ATG GGA TAG AGT GCA TCC AGT GCA TG-3' (SEQ ID NO:10:)

5'-GA CAG TGT AGA TAG ATG ACA GTC G-3' (SEQ ID NO:11:)

Probes generally may be of varying length, for example, 16–2000 base sequences but preferably are within the range of 20–100 bases in length, the shorter sequences being preferred because of faster reaction with the target. For ease of reference, the detecting probe is referred to herein as the B-probe while the capture probe is referred to as the A-probe.

The probe may be bound to the platform in any convenient fashion, e.g. by covalent bond or by receptor-ligand interaction. Usually this can be most advantageously accomplished by reaction between streptavidin (SA) and biotin. Preferably, as noted below, the probe is biotinylated and joined to a complex comprising the platform and labels capped with streptavidin.

Conventional ECL labels are used herein, the primary difference being the attachment of a multiple number of such labels to the platform, e.g. more than 2, preferably 10 to 20 attached to the BSA platform. Such labels comprise electrochemiluminescent compound, including organic and organometallic compounds. Organic compounds which are suitable electrochemical labels include, for example, rubrene and 9,10-diphenyl anthracene. Many organometallic compounds are suitable electrochemical labels, but of particular use are Ru-containing, such as Ruthenium II trisbipyridine chelate, and OS-containing compounds. Labels useful in the presently disclosed invention can be found in U.S. Pat. No 5,310,687, the contents of which are incorporated herein by reference.

These labels are stable for long periods and may be attached efficiently to a wide variety of chemical, biochemical, and biological materials. In addition, the labels are safe and relatively inexpensive. They give a highly characteristic signal and do not occur in nature. Measurements based on luminescence of such labels are sensitive, fast, reproducible and utilize simple instrumentation. The signal is generated repeatedly by each molecule of the label, thereby enhancing the sensitivity with which these labels may be detected.

The preferred electrochemiluminescent labels of the present invention are conveniently referred to herein as TAG. Various amounts of this label, or its equivalent, may be attached to the platform. The attachment may be carried out by covalently bonding the TAG label to the surface of the platform by, for example, NHS ester chemistry which will be known by those skilled in the art. Preferably, up to a 50-fold molar excess of TAG is used in the labeling reaction, although more or less than this amount may be used as the circumstances may require. After binding of the TAG or equivalent label, the complex is advantageously purified by, for example, molecular exclusion column with a molecular weight cutoff of 10,000.

In a particularly preferred embodiment of the invention, streptavidin is coated over the labels and the surface of the platform. This "capping" functions to minimize non-specific binding which might occur as a result of the number of labels present. Capping may be accomplished by incubating the TAG labeled biotinylated complex (which may be conveniently referred to as BSA-bio-TAG) with a 10-fold excess of streptavidin (SA) to form a complex of BSA-bio-TAG-SA where bio, BSA, TAG and SA have the meanings given earlier. It could also be anticipated that capping could be achieved by a particular type of platform having invaginations or other structures to achieve a capping result.

Binding SA to all biotins on the complex also serves to provide convenient binding sites for the biotinylated probes as mentioned earlier and further explained below. The biotinylated probes may be bound to the BSA-bio-TAG-SA complex by simply incubating in appropriate molar ratio under standard incubation conditions. The resulting complex, preferably after purification, is then ready to be used in an ECL assay in combination with the capture probe of the present invention.

While it is preferred to completely cover the BSA-bio-TAG complex with SA, it is possible to use BSA-bio-TAG which is only partially coated with SA.

The assay system for use herein also includes magnetic beads (as the solid phase) carrying an oligonucleotide probe which serves as the capture probe. Magnetic beads as conventionally used in ECL assay systems may be used. The nature and size of these beads can be varied as long as they are useful in the ECL system. As will be understood by those in the art, the beads must be of a size which permits them to interact with the electrode. DYNAL™ beads are polystyrene microparticles having an iron oxide core rendering them super para-magnetic having a 2.8 μm diameter are representative of the types of beads which may be used. Magnetic beads are hereinafter described "MB".

The beads also include a coating or other means for affixing the oligonucleotide capture probe to the bead. For example, the bead may be coated with streptavidin so as to bind and carry the oligonucleotide probe, the latter being biotinylated for reaction with the streptavidin. Alternatively, the bead may be biotinylated and the probe modified with streptavidin for attachment to the bead. Other alternatives or modifications are contemplated provided the result comprises a magnetic bead carrying an oligonucleotide probe for ECL use.

The oligonucleotide probe attached to the bead may be the same or different from the probe attached to the platform complex. Preferably the bead probe is an oligonucleotide which recognizes a specifically different portion of the target DNA or RNA from the platform probe.

The assay may be carried out in one or two steps. In the one step process, the preformed capped, multi-labeled complex (for example, BSA-bio-TAG-SA with oligonucleotide attached) is incubated in the ECL system with the target sample, and the capture probe containing SA coated magnetic beads, and oligonucleotide complementary to a sequence of the target. The incubation may be carried out for up to an hour after which time the measurement of the localized label at the probe indicates the presence of the target DNA or RNA in the ECL apparatus. A sensitivity of 1000–10,000 molecules of target analyte can be realized.

Significantly an effective signal is obtained even with the capped complexes because ECL is a field event and the molecular complex produces light when influenced by an electronic field even if the labels are covered by SA. It is also noted that the TAG moiety needs a turnover of the oxidant TPA used in the mechanism of FIG. 1 in order to produce a measurable signal. Accordingly, proper circulation must be assured so the TPA precursor can diffuse at a sufficient rate to the TAG molecule in the capped complex. The capped BSA-bio-TAG-SA complex referred to above has been found to provide an effective pathway for TPA diffusion while still blocking non-specific binding. This may be due to the globular nature of the SA providing channels to the TAG.

In the two step process, the test sample is first incubated with either the detecting probe (B-probe) or the capture probe (A-probe) after which the other probe is added to the system to complete the assay. For example, the sample DNA is contacted with a first biotinylated capture probe (A-probe) along with streptavidin (SA) magnetic beads under suitable conditions to form a DNA-A-probe-SA-MB (magnetic bead) complex. The DNA is hybridized to the A-probe which is bound in turn to the streptavidin coated MB. The biotinylated detector probe (B-probe) having a separate specificity for the DNA sample from that of the capture probe, is premixed with streptavidin and biotinylated bovine serum albumin labelled with TAG to form a complex comprising oligonucleotide probe and BSA-bio-TAG-SA where the labeled BSA is linked to streptavidin which in turn is linked to the oligonucleotide probe. This premixed complex is then introduced to the sample in a second step under conditions suitable for the hybridization of the second probe to the bound DNA sample. The resulting complex is then subjected to electrochemical energy sufficient in the ECL device to obtain an electrochemiluminescence signal which is measured.

Preferred embodiments of the presently disclosed invention may be further understood with reference to FIGS. 4–8 and the following.

Figure 4:
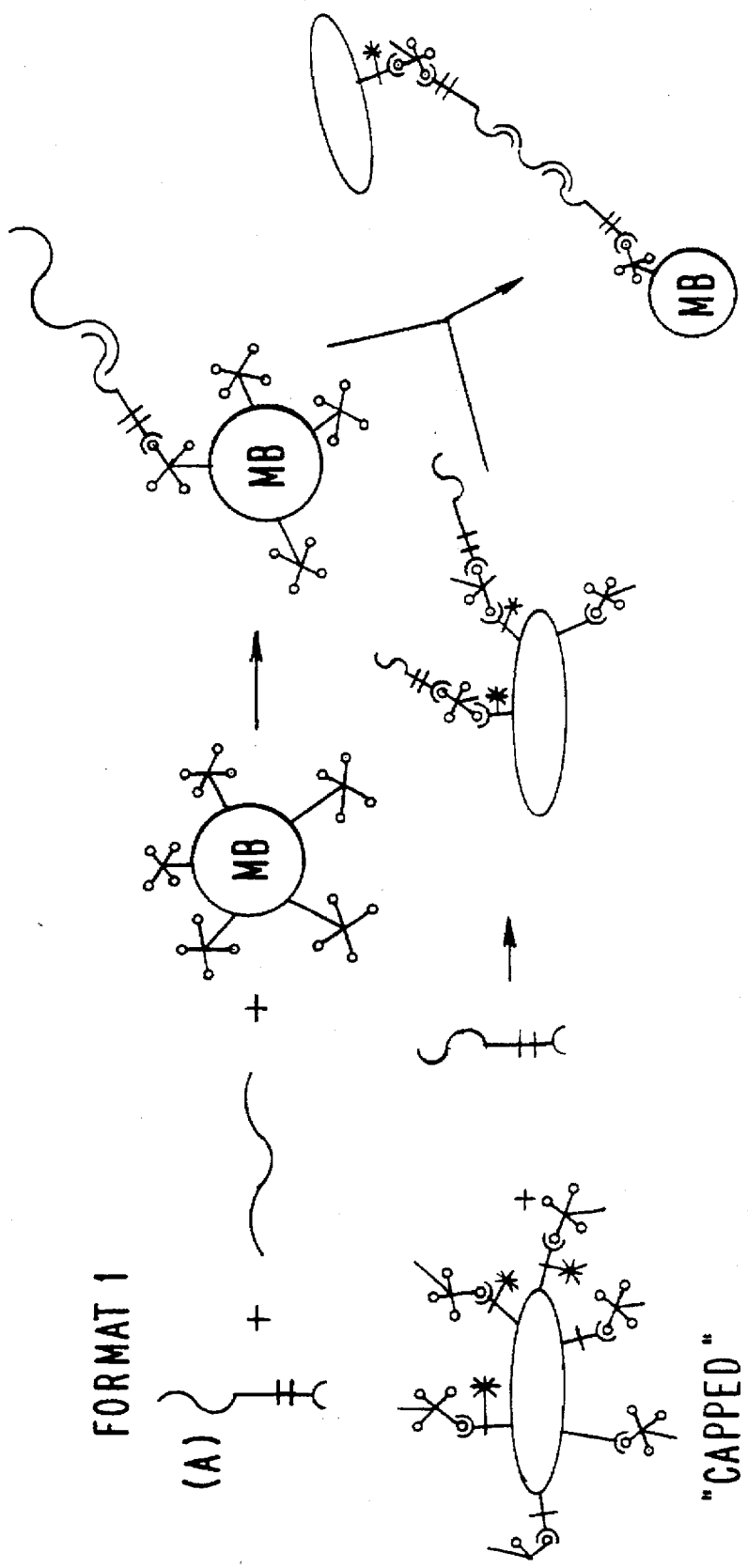

Format 1 shown schematically in FIG. 4, builds an assay from the solid phase up. The first step is the capture of analyte onto the magnetic bead through interaction with the first probe. In the second step, the signal producing complex and second probe which complexed prior to the assay are added to detect the presence of the analyte-probe-magnetic bead complex.

One skilled in the art will appreciate that the advantage of this scheme is to potentially provide a 1-step format since all binding points are unique. Data from these experiments described in Example 1, below indicated a sensitivity of $10^4$ copies of analyte per assay. Dynamic range was 6+ logs with an extremely shallow slope from $10^4$ to $10^8$ copies which rose sharply as the number of copies increased. Variation in the negative control was very low (0.75% CV in one experiment).

Figure 5:
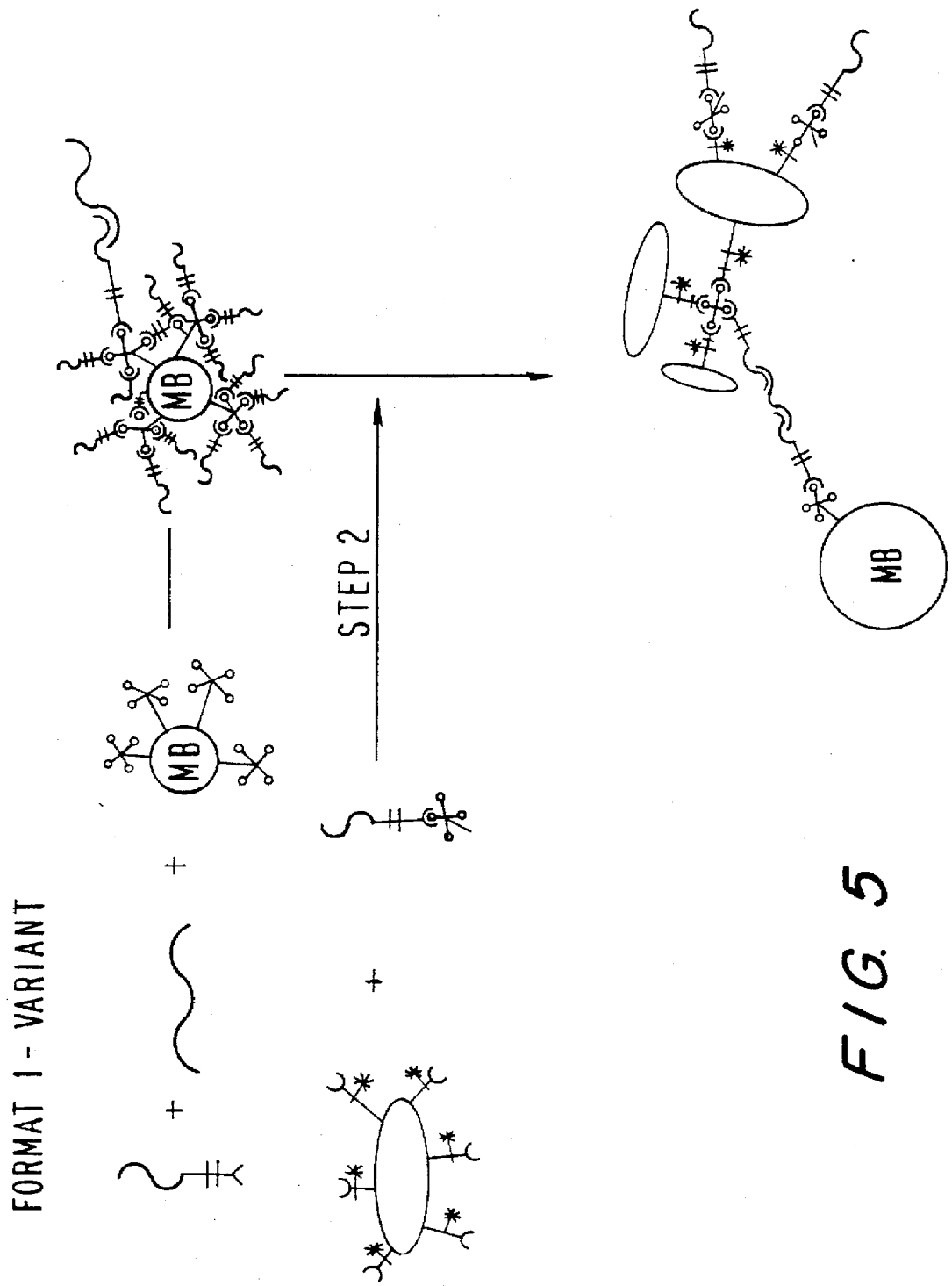
FIGS. 5–8 are schematics, respectively, of Format 1 (variant), Format 2, Format 3 and Format 4.

A variation of Format 1 is shown in FIG. 5 wherein the complex is not coated with SA. In this Format, target DNA is captured onto the magnetic bead (MB) by a biotinylated capture probe, in the first step. An abundance of biotinylated probe is necessarily added in the first step to avoid directly binding the BSA-bio-TAG in the second step. In the second step, BSA-bio-TAG is added along with a pre-mix of second detector probe bound to SA. This method yields the highest ECL signals, however, non-specific binding must be carefully controlled by means known to those skilled in the art.

As demonstrated in Example 3 below, a linear plot of signal, increasing with an increase in analyte, was obtained. Sensitivity of $10^4$ copies of analyte per assay was generated with a dynamic range going to $10^8$ and leveling. A low variation (CV=3–4%) in the negative control could be obtained if low concentrations of magnetic beads were used. This format, though rigid in its control, proved that an uncapped ECL complex (i.e., having no SA cover) could produce acceptable results. This format also illustrated the disadvantage of an uncapped TAG complex. This disadvantage was in the high non-specific binding that occurs with an uncapped complex. The high signal generated may have been a result of this. Overall, a signal-to-noise was not as good as a capped complex.

Figure 6:
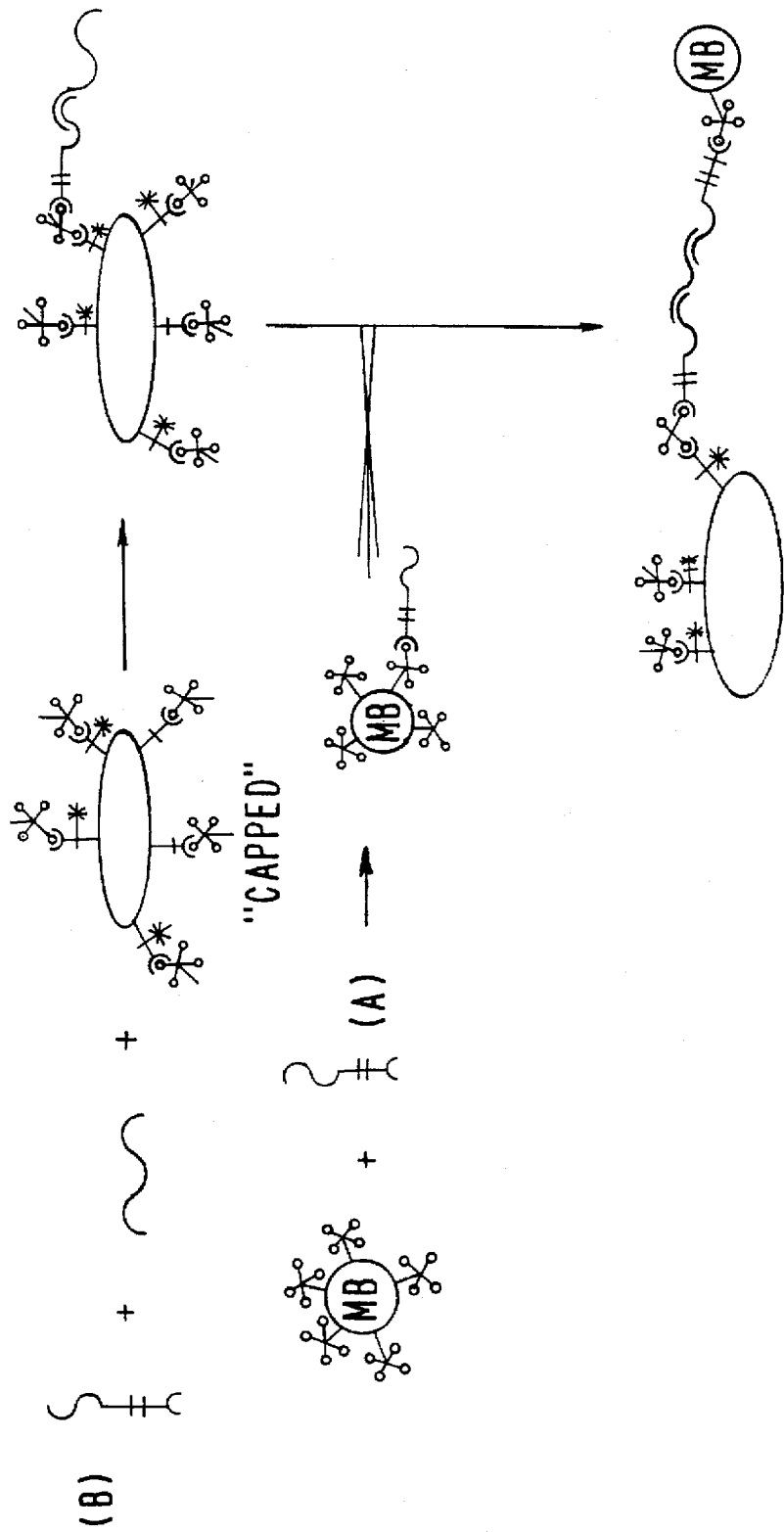

A second format (Format 2) is schematically depicted in FIG. 6. Although similar to Format 1 in that the measuring reaction is performed in two steps, Format 2 differs in that the BSA-bio-TAG-SA complex is introduced directly in the first contacting step and the streptavidin coated magnetic beads are introduced in a second step. The first contacting step results in the formation of a DNA/B-probe/BSA-bio-TAG-SA complex wherein the sample DNA hybridizes to the B-probe which in turn attaches itself to the BSA-bio-TAG-SA complex through the streptavidin moiety. The second contacting step results in the formation of complex between the second biotinylated probe (capture probe) and the streptavidin bead. The attachment of the probe and the bead is through the streptavidin-biotin interaction. The measurement of the electrochemiluminescent signal and its generation is analogous to the first format.

This scheme is essentially the reverse of Format 1. The target DNA was captured onto the ECL complex (BSA-bio-TAG-SA) after hybridizing to the biotinylated detector probe. The second step was the addition of the capture probe and SA coated magnetic bead to the system.

This method proved less efficient than Format 1. Variation of the negative control (tRNA) was significantly higher than in Format 1. Still, a sensitivity of $10^4$ copies of analyte per assay with a range extending to $10^{11}$ was achieved (significant to only 1 standard deviation from the negative control, CV=6%). (Data not shown).

Figure 7:
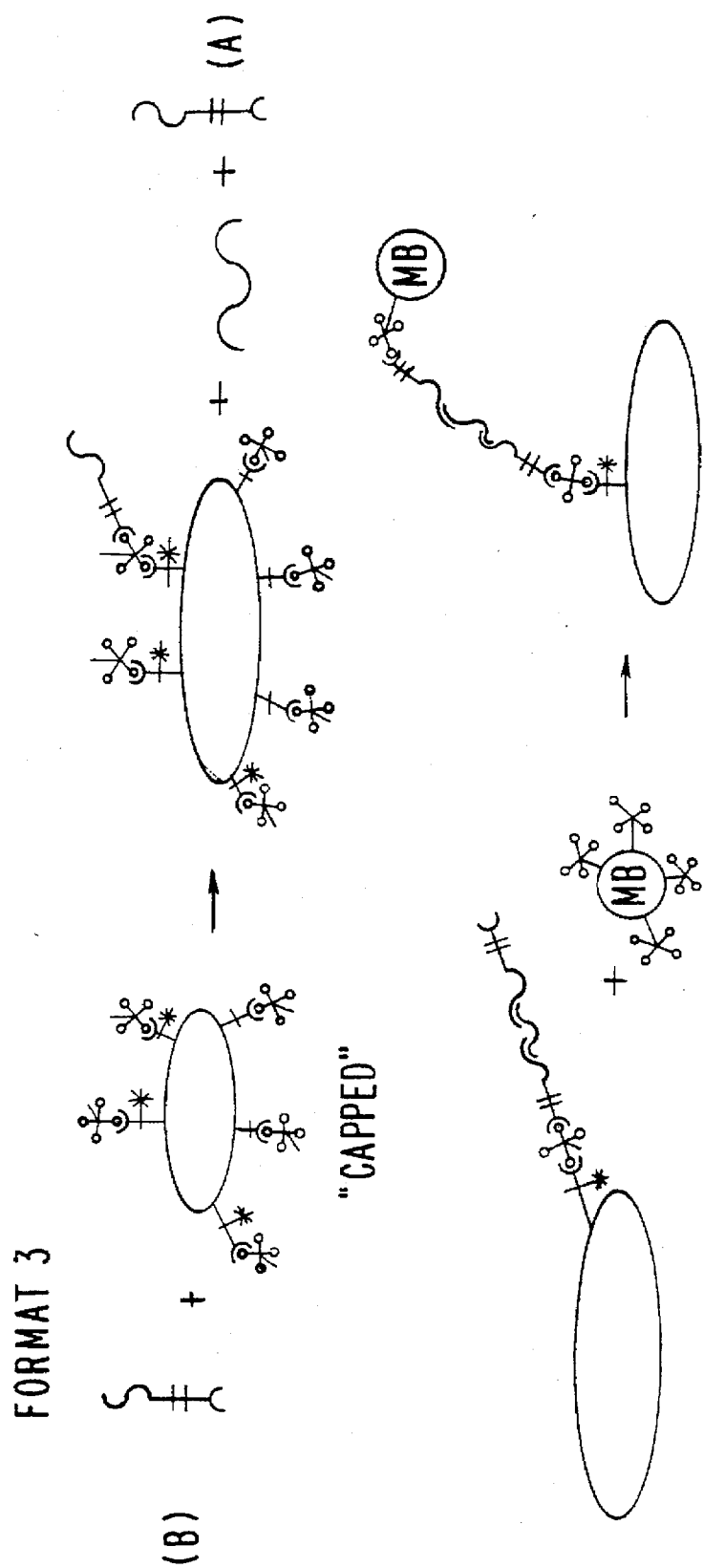

A third Format of the instant invention is depicted in FIG. 7. Format 3 reflects another variation of the assay where the measuring reaction is performed in two steps. In the first contacting step, all components, except for the streptavidin coated beads are introduced with the caveat that the B-probe and the BSA-bio-TAG-SA platform molecule are premixed to form an oligonucleotide/BSA-bio-TAG-SA complex to allow the biotinylated probe to attach to the platform molecule through the streptavidin moiety. In the second contacting step, the SA coated magnetic beads are introduced to permit the formation of the complex which is measured in the manner set forth above.

As noted in Example 5, good results were obtained from Format 3 where an ECL complex/probe hybridization product was created in the first step. This product was then captured onto the SA coated magnetic beads in the second step. A pre-mix of the ECL complex (BSA-bio-TAG-SA) and biotinylated probe was made which facilitated the specific binding of all reactants.

A sensitivity of $10^4$ copies of analyte per assay with a range extending beyond $10^{10}$ copies was found in these experiments. Variation in the negative control (tRNA) was acceptable, about 3-4% CV and the plot of the slope of this data exhibited a relatively linear characteristic.

Figure 8:
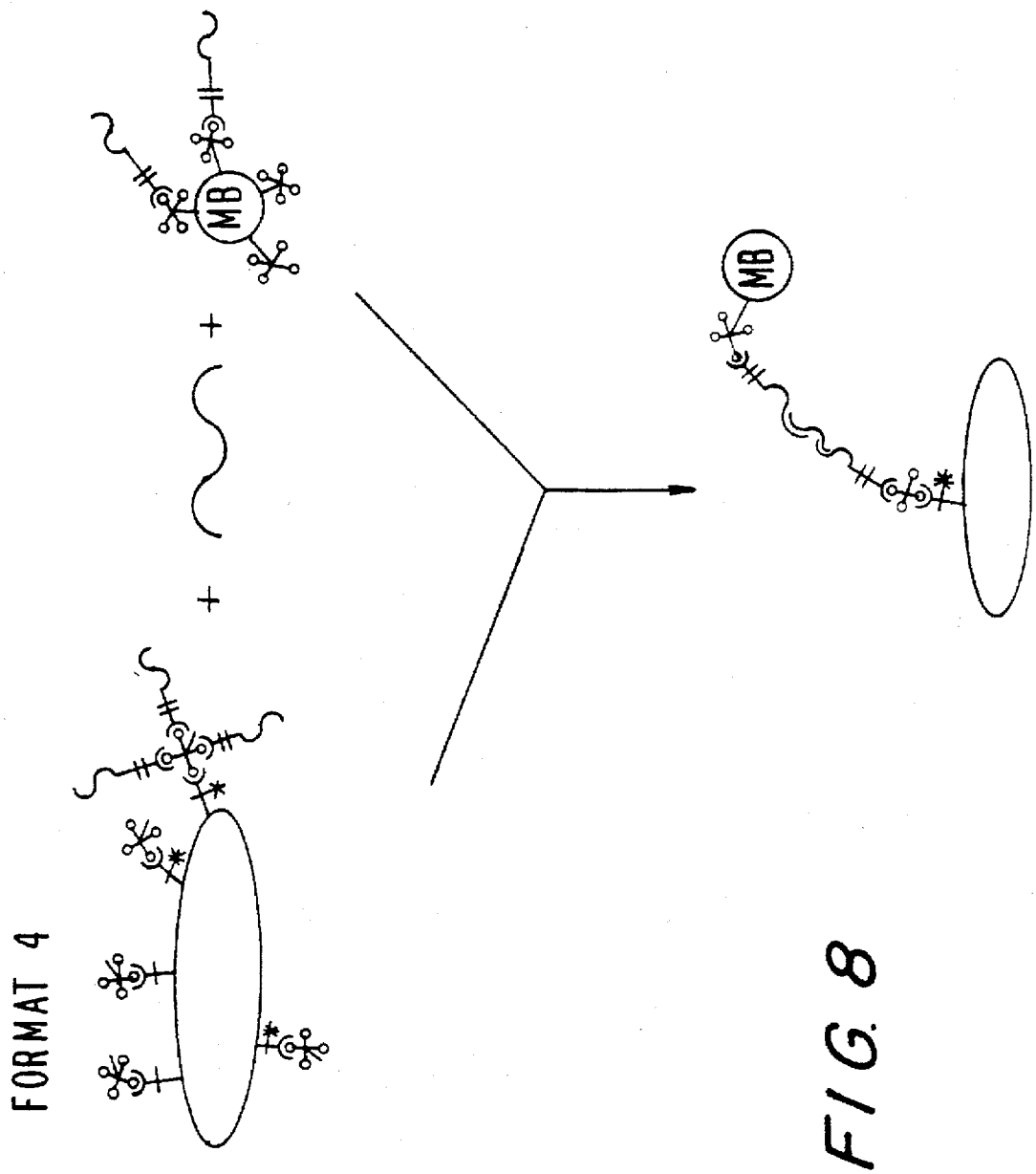

Finally, in a fourth Format, depicted in FIG. 8, the reaction scheme differs from the other three Formats in that the measuring reaction is performed in one contacting step and the only one separate biotinylated probe is used with the second probe having been previously attached to the BSA complex via SA-biotin binding. The complex which is measured, therefore, is formed through the hybridization of at least two probes to the sample DNA. One of the probes was attached to the BSA-bio-TAG-SA platform molecule through the streptavidin moiety on the platform molecule. The second hybridized biotinylated probe attaches itself through streptavidin to the magnetic bead.

As explained in Example 6, one group of experiments testing this fourth Format yielded extraordinary results. A complex of BSA-bio-TAG was incubated with an excess of SA, then purified. Afterwards, this complex was incubated with a 10-fold excess of biotinylated probe which yielded a theoretical number of probe binding sites of 10 per complex.

Excellent results were obtained in an experiment in which a sandwich hybridization assay was performed in one step. To accomplish this, the BSA-bio-TAG-SA complex was pre-mixed with the biotinylated C probe (Artificial sequence which is complementary to a region in the CA target DNA) to form a BSA-bio-TAG-SA-C probe reagent. The assay was then performed by incubating this complex with the target DNA (a 60 base synthetic CA sequence of the HIV-1 gag gene), a biotinylated A probe, Dynal M280 SA coated 2.8 µm paramagnetic beads and tRNA. Incubation was done for 25 min with agitation at room temperature.

To formulate the oligo C probe/BSA-bio-TAG-SA complex reagent, the BSA-bio-TAG-SA complex was incubated with the biotinylated C oligonucleotide probe at specific molar ration of 10:1. This process resulted in the BSA-bio-TAG-SA-bio-C probe reagent. Relative copy numbers of the complex to the probe were $10^{10}$ molecules of the complex to $10^{11}$ copies of the probe.

10 uL of target DNA was made in increasing quantity of $10^3$ to $10^8$ copies per tube. To these samples, the BSA-bio-TAG-SA-C probe complex, the biotinylated A probe and Dynal SA coated M280 paramagnetic beads along with yeast was added. This mixture was incubated for 25 min at room temperature with agitation. After this period, the samples were read on the IGEN ORIGEN Analyzer.

Cutoff value and significance of results were calculated as done previously (mean plus two standard deviations of negative control sample). The slope of the plotted data indicated an increase in signal of three orders of magnitude for the five order of magnitude increase in analyte. Sensitivity of this assay was $10^3$.

The invention is further illustrated by the following non-limiting examples which are given only for illustrative purposes.

EXAMPLE 1

(Conventionally Labelled Probe)

Hiv-1 gag Gene DNA ASSAY
Magnetic Beads

Dynal M-280 streptavidin coated magnetic beads were procured from Dynal, A.S. (Oslo, Norway). The beads were suspended in Origen assay buffer to give a concentration of 20.0 µg/50 µL prior to use. The value of 20.0 µg of beads per sample was found to be an optimum value for the assay (data not shown).

Oligonucleotide Probes and Synthetic Target DNA

The following oligonucleotide probes, and synthetic target DNA samples were used in the assays described: The BA target is a 60 base fragment from the gag region of HIV1. DNA and RNA oligonucleotides were made for the BA sequence. Albiotin probe was a 25 base oligo probe, biotinylated at the 5' end, homologous to a region near the 3' end of the BA sequence. B2TAG probe was a 28 base fragment, ECL labelled at both the 5' and 3' ends, homologous to a region at the 5' end of the BA target.

The olignucleotides were biotinylated at the 5'-NH$_2$ using biotin NHS-ester and Origen labelling was introduced by Origen-NHS ester using standard labelling protocols at the 5' site and a phosphoramidite reagent at the 3' site. The labelled oligonucleotides were purified by Biogel-P6 column chromatography. The oligonucleotides were also purified by Biogel-P6 column polyacrylamide gel chromatography, and high performance liquid chromatography. Both single and double Origen-labelled gel purified probes have been used in the assays with equivalent results.

Instruments

IGEN ORIGEN® analyzers mounted with platinum cells were used. Internal temperatures of the instruments were set at 35° C. incubations at 42° C. for DNA hybridizations were performed in a shaker incubator. Hybridization Buffer (for dilutions of oligo probes and DNA)

1× SSPE

10× Denhardts (1% Ficoll, 1% PVP, 1% BSA)

5 0.1% SDS IGEN Assay Buffer (for dilutions of beads and assay mix)

Essentially a phosphate buffer of neutral pH containing TPA and Triton X-100.

Sequences

Albiotin:

5'bio-TGT TAA AAG AGA CCA TCA ATG AGG A-3' (SEQ ID NO: 6)

B2TAG:

5'TAG-GA ATG GGA TAG AGT GCA TCC AGT GCA TAG-3' (SEQ ID NO: 7)

BA Target:

5'-CAT GCA CTG GAT GCA CTC TAT CCC ATT CTG CAG CTT CTT CAT TGA TGA TGG TCT CTT TTA ACA-3' (SEQ ID NO: 5)

Oligo Probe/Capture Probe—Standard Assay

The general protocol for performing an ORIGEN oligo probe bead capture assay is executed in two phases. The low fluid volume hybridization/bead capture is performed in one step. This is following by the addition of assay buffer to bring the reaction mixture to the required volume and concentration for reading in the ORIGEN Analyser.

The standard assay protocol used the AB probe set. A and B Probes are specific for regions in the gag gene of HIV-1. Oligonucleotide probes were synthesized using an Applied Biosystems nucleic acid synthesizer and labelled by standard methods. (For example by phosphoramidate or NHS ester labeling of amine of like modified probes.) The A1-biotin probe was labelled with one molecule of biotin while the B2-ECL probe was labelled with two molecules or the Origen (Rubpy) label ("TAG" label). Concentrations of each probe in the assay was $10^{12}$ molecules per reaction.

Standard Assay Protocol

1. Add the following in order together:

10 µL of test nucleic acid is aliquoted to the assay tube.

20 µL Abio probe/B2TAG (1.4 ug/mL each)

50 µL streptavidin coated magnetic beads (Dynal, 20 ug)

2. Mix on a rotary shaker, 15 min at 42° C.

3. Add 200 µL of AB

4. READ SAMPLE Results:

One Step Test—Standard Curve

Under the standard assay conditions and buffers described above, BA DNA as well as RNA (data now shown) test samples were assayed in the ORIGEN system. Log concentrations of DNA ranged from $10^6$ to $10^{13}$ molecules per 10 uL aliquot used in the assay. Probe concentration was $10^{12}$. Triplicate samples were assayed in three different instrument runs.

Figure 9:
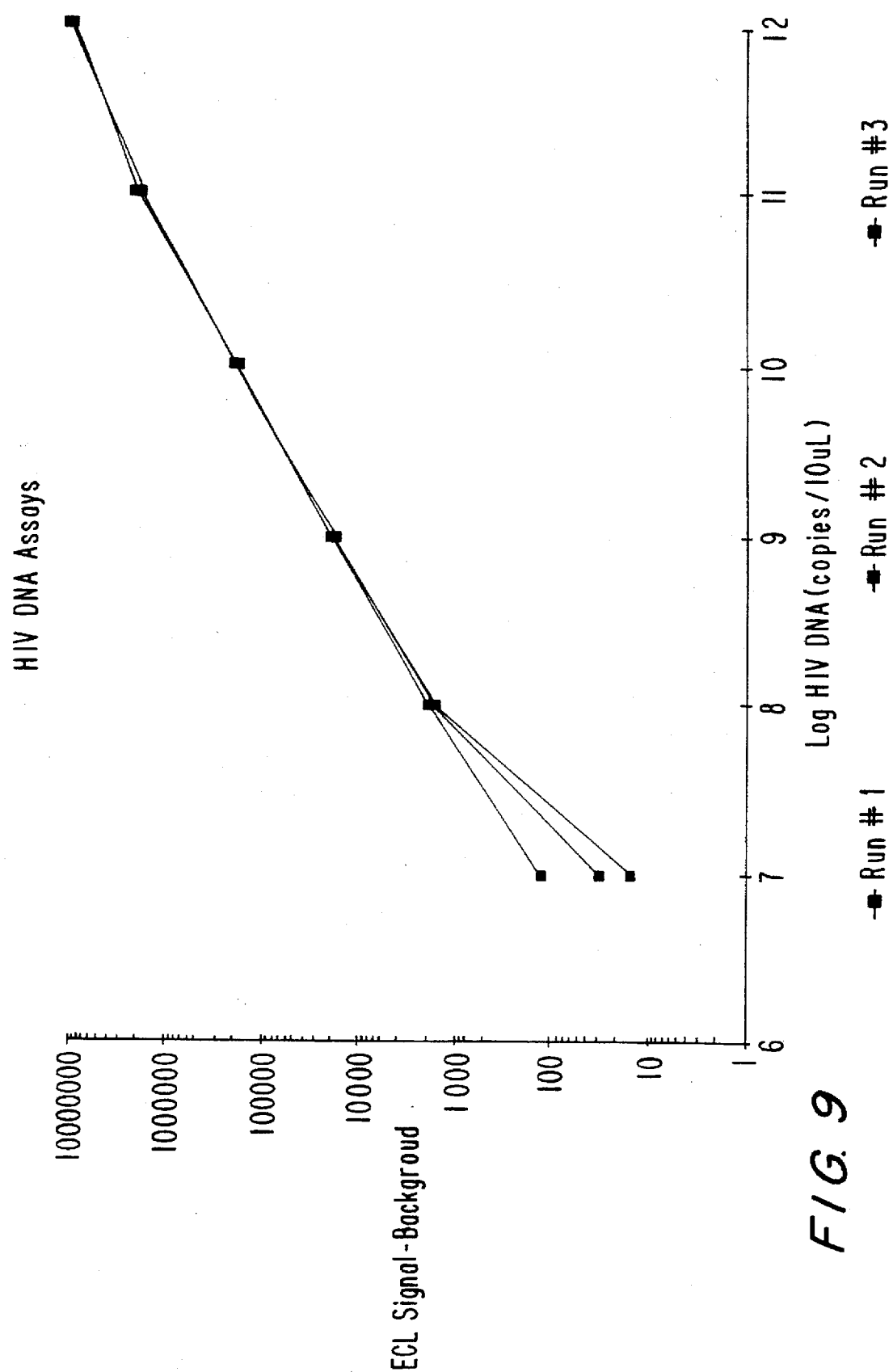
FIG. 9 (prior art) is a log-log plot of experimental data obtained in example 1 where the 1) BA target is a 60 base pair fragment from the gag gene region of HIV 1, 2) A1 biotin probe is a 25 base oligo probe, biotinylated at the 5' end and the B2 TAG probe was a conventionally prepared 28 base fragment where ECL is labelled at both the 5' and 3' ends. The three plots [■] reflect runs on triplicate samples.

A standard curve was plotted with this data (FIG. 9). A linear plot was developed on a log-log graph using this data. The assay was able to detect $10^7$ molecules of the target DNA. The dynamic range was shown to be 5 orders of magnitude. Signal at $10^{12}$ molecules approached the maximum of the system. There was a marked decrease in signal at $10^{13}$ molecules. This is most probably due to excess unbound target nucleic acid molecules binding labelled probes. The slope of the plot approached 1 with excellent linearity.

EXAMPLE 2

The following general procedures were employed throughout.

Preparation of the BSA-bio-TAG-SA Complex 200 ug BSA-biotin (Sigma, approx 11 biotin's per BSA molecule) was made up in 250 uL phosphate buffered saline (PBS buffer). 100 ug of TAG-NHS ester (ruthenium (II) tris(bipyridyl)-NHS, IGEN, Inc.) was reconstituted in 50 uL of dry DMSO. The TAG-NHS ester was then added swiftly to the BSA-bio while vortexing. This mixture was incubated with shaking at room temperature (RT) for 60 min, while wrapped in aluminum foil. The reaction was halted after incubation with the addition of 50 uL 2M glycine and further mixing for 10 min at room temperature (RT). This step produces the BSA-bio-TAG complex.

The TAG-NHS protocol is known to have a very high degree of reliability, assuring that every BSA-bio can be reacted with TAG.

Un-reacted TAG-NHS and glycine were then removed from the BSA-bio-TAG complex by centrifugation through an Amicon Centricon-30 spin column (30,00 MW exclusion column, Amicon Corp.). The entire volume of reaction mix was added to a Centricon-30 and centrifuged in a low speed table top centrifuge at approximately 1500×g for 30 min (or until only 50–75 uL of liquid remains in the spin column) as per well known protocols detailed in the manufacturer's product insert. 500 uL of fresh PBS was then added to the column and centrifugation performed again. This washing/buffer exchange procedure was repeated a minimum of three times and a maximum of five. Finally, the BSA-bio-TAG was taken up in a final volume of 1000 uL PBS.

At this point, the BSA-bio-TAG could be used for various experiments, stored at 4° C. or further complexed with streptavidin (SA).

Complexing with SA produces the "capped" BSA-bio-TAG-SA. This was accomplished by the following procedure. 500 uL of BSA-bio-TAG (100 ug, from above) was placed in a 2 mL vial. To this, 1 mL of 1 mg/mL streptavidin (SA, Sigma) is added and allowed to incubate, with mixing, at RT for 1 hr. The SA was in at least 10× molar excess relative to the BSA-bio-TAG. The result of this process was to produce the BSA-bio-TAG-SA complex, completely "capped" with SA. This complex was purified using an Amicon Centricon-100 (100,000 MW exclusion) column by well known procedures, outlined above. The final BSA-bio-TAG-SA complex was made 100 ug/mL in PBS and stored at 4° C. in the dark.

Preparation of BSA-bio-TAG-SA-probe

The convenience of SA/biotin binding was used in order to attach oligonucleotide probes to the BSA-bio-TAG-SA complex. Many other means would have been available to accomplish this. Synthetic oligonucleotide probes were obtained commercially with a biotin molecule covalently bound to the 5' end.

A 10-fold molar excess of biotinylated probe, specific for the target DNA in question, was incubated with the BASbio-TAG-SA complex for a minimum of 30 min in PBS or hybridization buffer. As the bio/SA binding is extremely efficient, at the concentrations used, no purification of this complex was necessary. In general, 0.1 ug/mL of a 22 base biotinylated oligo probe was incubated with 100 ng/mL of the BSA-bio-TAG-SA complex. This gave a ratio of 10 probe molecules for 1 molecule of complex. Storage of this product was at 4° C. in PBS.

Preparation of Magnetic Beads Coated with SA

Commercially available. Dynal M-280, streptavidin coated, 2.8 μm magnetic beads (Dynal, Norway).

Preparation of Biotinylated Probe

Oligonucleotide probes used were commercially synthesized by routine phosphoramidite methods and made to have one biotin molecule covalently linked to the 5' end.

EXAMPLE 3

Format 1 ECL Assay—2 Step: BSA-bio-TAG-SA-bio (Detector Probe) Combined with MB-SA-bio-(Capture Probe)-analyte.

A schematic of Format 1 is shown in FIG. 4.

The BSA-bio-TAC-SA complex was incubated with the B biotinylated oligonucleotide probe (specific for a region in the HIV-1 gag gene) in order to make a BSA-bio-TAG-SA-bio-probe complex for binding target DNA. This reagent was generated by taking 10 uL of 100 ng/mL of the BSA-bio-TAG-SA and mixing it with 10 uL of 100 ng/mL of the B biotinylated oligo probe at room temperature for 1 hour. This complex was then used without purification as the number of biotin binding sites exceeded the biotin label probe copy number.

A DNA probe sandwich hybridization assay was performed in two steps. In the first step, 10 uL of target DNA was incubated with 10 uL of biotinylated capture probe ("A", specific for a different region in the HIV-1 gag gene) at 100 ng/mL, 10 ug of Dynal M280 streptavidin coated paramagnetic beads (2.8 um nominal diameter) in 25 uL PBS buffer, and 10 uL of tRNA (100 ug/mL). Incubation was for 20 min at room temperature (note that oligo probes are highly sequence specific and so hybridizations could be done at RT followed by the instrument cycle at 37° C.).

To this mixture, the 20 uL of BSA-bio-TAG-SA-bio-probe complex was added and incubation allowed to continue for an additional 20 min at RT. After this, 20 uL of a phosphate buffer was added to the mixture and the material assayed on the IGEN ECL (ORIGEN) Analyzer.

Figure 10:
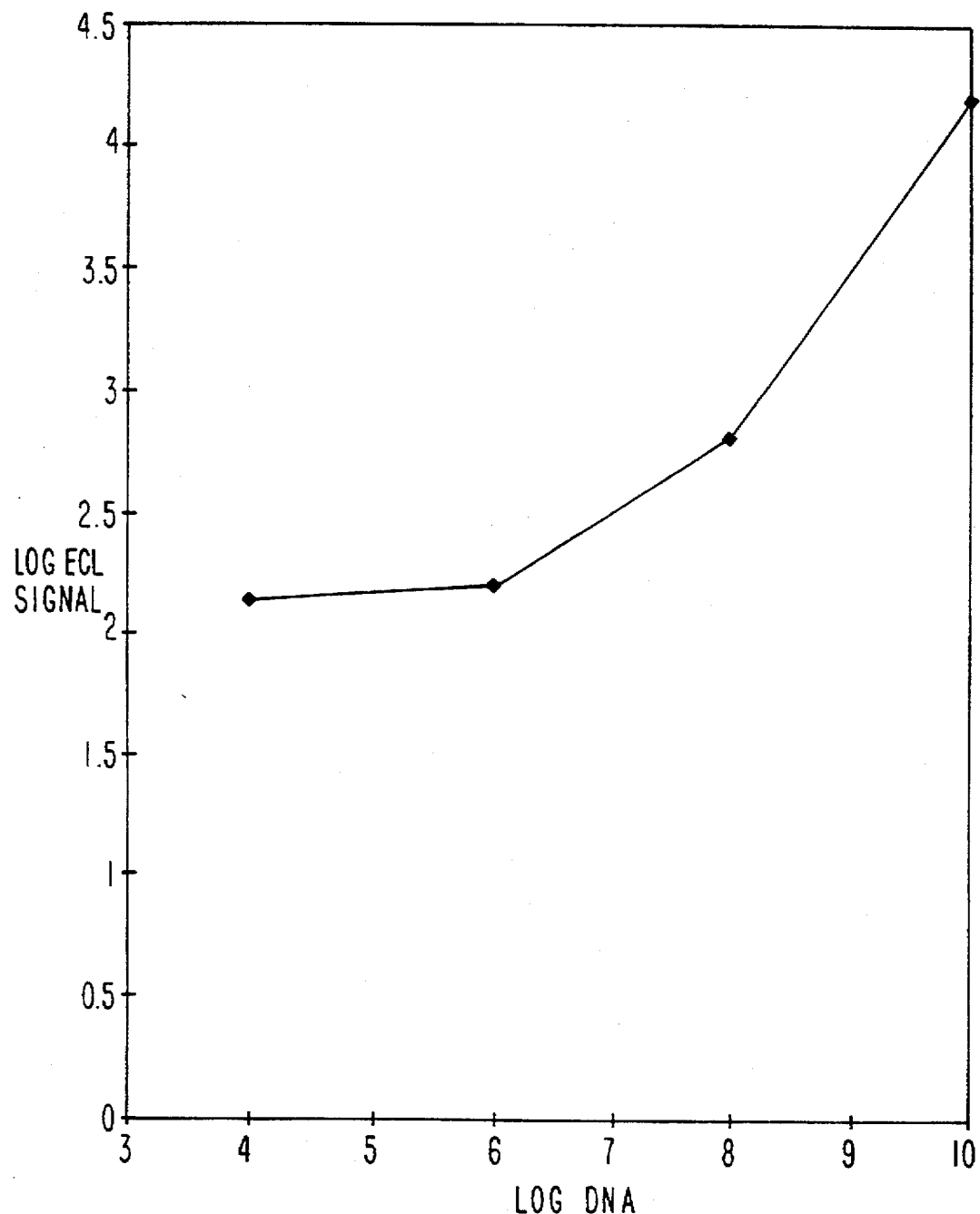
FIGS. 10–13 are log-log plots of the experimental data obtained in examples 3–6, respectively.

The resulting data indicated a sensitivity of 10,000 molecules of target DNA with a dynamic range of 6 orders of magnitude. The slope of the curve was initially shallow on a log-log plot of signal versus analyte copy number, then linear from $10^6$ to $10^{10}$ copies of target DNA. See FIG. 10. Significance was determined by using a cutoff value of the mean plus two standard deviations (mean +2SD) of the negative control samples (10 uL of yeast tRNA at 100 ug/mL).

EXAMPLE 4

Format 1 ECL Assay—(Variant)—2 Step Process Without Capping

A schematic of Format 1 (Variant) is shown in FIG. 5.

The nature of an uncapped BSA-bio-TAG complex was tested in this experiment. The BSA-bio-TAG complex was the same one used in other experiments but without incubation with SA to "cap" the complex.

A two step sandwich hybridization experiment was performed. In the first step, 10 uL target DNA, 20 uL biotinylated A probe (1.4 ug/mL) and 4 ug (in 10 uL PBS) Dynal M280 magnetic beads were incubated together along with 10 uL of yeast tRNA (100 ug/mL). Incubation was performed at room temperature for 30 min with mixing. After this, 20 uL of the BSA-bio-TAG complex (0.1 ug/mL) and 10 uL of a pre-mix of biotinylated B probe and SA (0.01 ug/mL and 1.0 ug/mL respectively) were added. Incubation was continued for an additional 30 min with mixing. 200 uL of a phosphate buffer was added to each assay tube and the samples read on the IGEN ORIGEN Analyzer.

Figure 11:
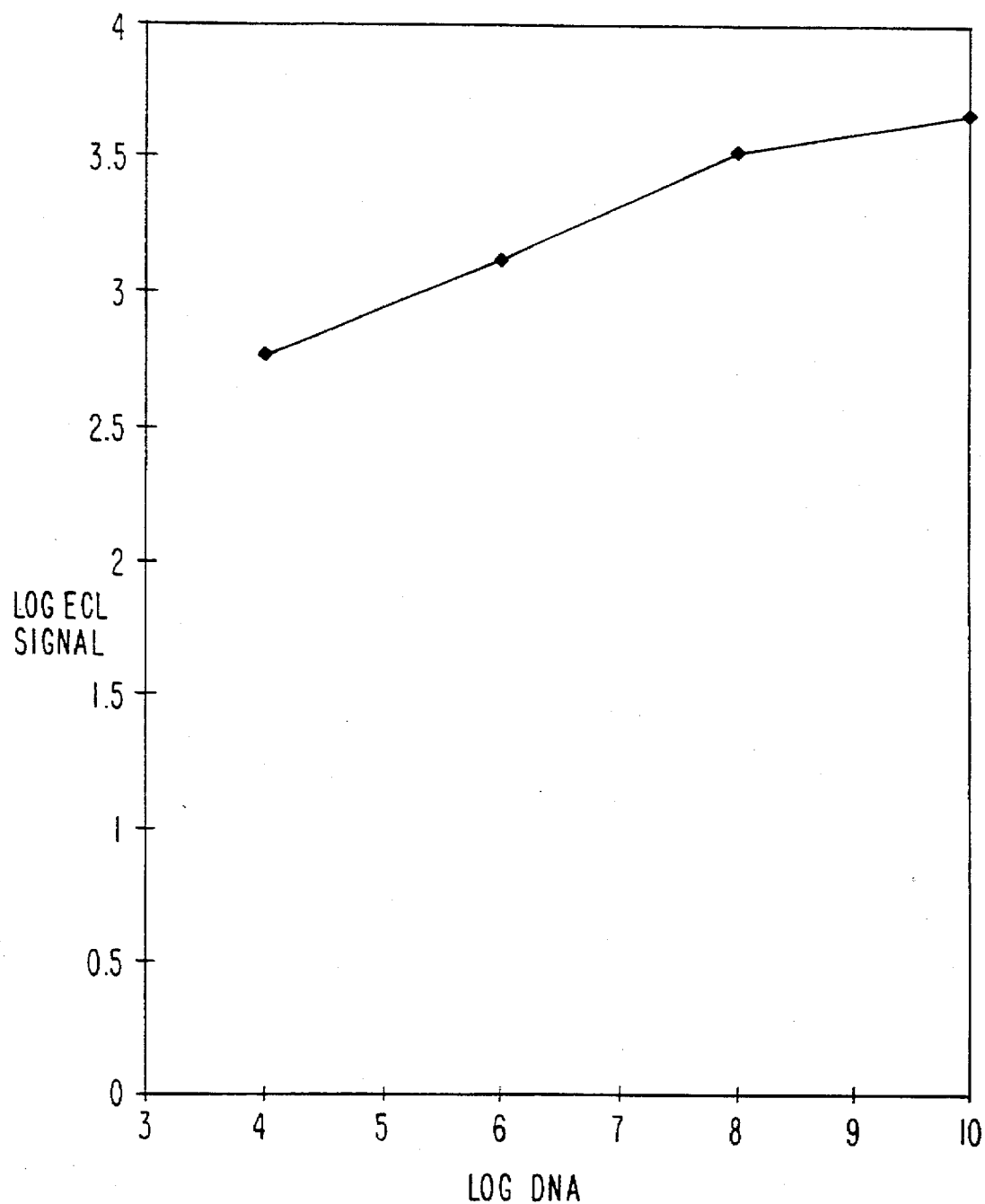

A sensitivity of 10,000 molecules of target DNA was found with sample dynamic range extending to $10^{10}$ molecules. The background in this experiment was approximately 8–9 fold higher than in the experiments using the "capped" complex. The slope of the plotted data was very shallow indicating a one order of magnitude increase in signal over the six order of magnitude increase in analyte. See FIG. 11.

EXAMPLE 5

Format 3 ECL Assay—2 Step: BSA-bio-TAG-SA-bio-(Detector Probe)-analyte-(Capture Probe)-bio Combined with SA-MB A schematic of Format 3 is shown in FIG. 7.

Another iteration of the method was to bind the biotinylated B probe to the BSA-bio-TAG-SA complex first and then perform a sandwich hybridization assay in two steps. In this example, the BSA-bio-TAG-SA-B probe, target DNA as well as the biotinylated A probe are incubated together. The second step was to add the SA coated magnetic beads in order to put the assay in the ORIGEN Analyzer.

The BSA-bio-TAC-SA complex was incubated with the B biotinylated oligonucleotide probe (specific for a region in the HIV- 1 gag gene) in order to make a BSA-bio-TAG-SA-bio-probe complex for binding target DNA. This reagent was generated by taking 10 uL of 100 ng/mL of the BSA-bio-TAG-SA and mixing it with 10 uL of 100 ng/mL of the B biotinylated oligo probe at room temperature for 1 hour in PBS. This complex was then used without purification as the number of biotin binding sites exceeded the biotin label probe copy number. Relative copy numbers of the complex to the probe were $10^{10}$ molecules of the complex to $10^{11}$ copies of the probe.

A sandwich hybridization assay was performed in two steps. In step 1, the BSA-bio-TAG-SA-B probe, target DNA as well as the biotinylated A probe are incubated together along with tRNA. Concentrations of reactants and volumes are the same as in example 2. Incubation was allowed to continue for 30 min and then 10 ug of Dynal SA coated M280 paramagnetic beads were added in 25 uL volume of a phosphate buffer. Incubation was continued for an additional 30 min and then 200 uL of a phosphate buffer added and the assay read on the IGEN ORIGEN Analyzer.

Figure 12:
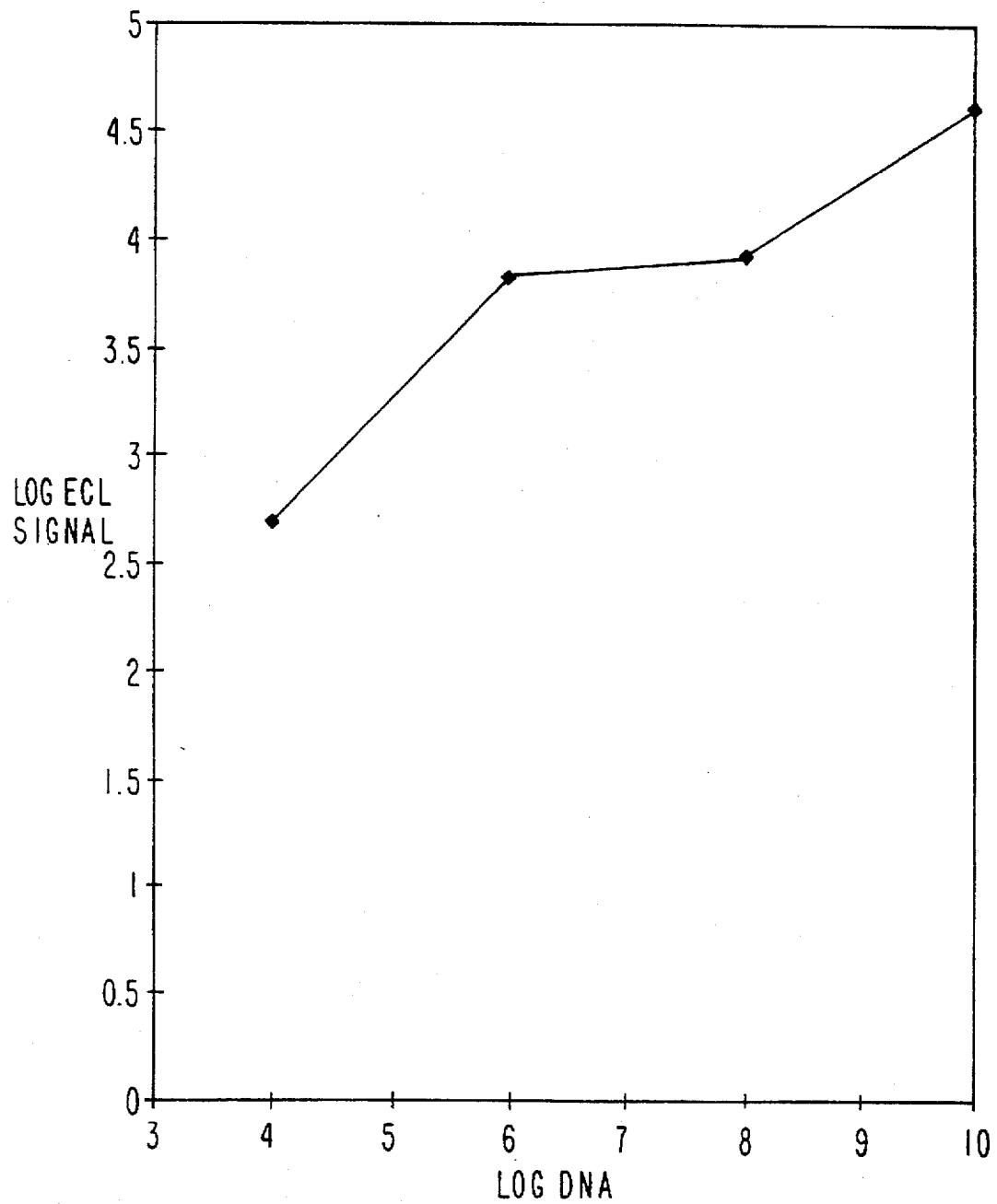

Significance of results was calculated as done previously. The data indicated a sensitivity of 10,000 molecules of the target DNA with a range extending to $10^{10}$ molecules (last concentration tested). The slope of the plotted data was shallow, having an increase in signal of two orders of magnitude for the six order of magnitude increase in analyte. See FIG. 12. This may have been due to complexing of the analyte with the assay reactants because of multiple binding sites on the BSA-bio-TAG-SA-Probe complex.

EXAMPLE 6

Format 4 ECL Assay—1 Step: BSA-bio-TAG-SA-bio-(Detector Probe) Mixed with Analyte and MB-SA-bio-(Capture Probe)

A schematic of Format 4 is shown in FIG. 8.

Extraordinary results were obtained in an experiment in which a sandwich hybridization assay was performed in one step. To accomplish this, the BSA-bio-TAG-SA complex was pre-mixed with the biotinylated C probe to form a BSA-bio-TAG-SA-C probe reagent. The assay was then performed by Incubating this complex with the target DNA (a 60 base synthetic CA sequence of the HIV-1 gag gene), a biotinylated A probe, Dynal M280 SA coated 2.8 um paramagnetic beads and tRNA. Incubation was done for 25 min with agitation at room temperature.

To formulate the C probe/BSA-bio-TAG-SA complex reagent, the BSA-bio-TAG-SA complex was incubated with the biotinylated C oligonucleotide probe (specific for an artificial sequence of DNA) at specific molar ration of 10:1. This process resulted in the BSA-bio-TAG-SA-bio-C probe reagent. This reagent was generated by taking 10 uL of 100 ng/mL of the BSA-bio-TAG-SA and mixing it with 10 uL of 100 ng/mL of the biotinylated C oligo probe at room temperature for 1 hour in PBS. This complex was then used without purification as the number of biotin binding sites exceeded the biotin label probe copy number. Relative copy numbers of the complex to the probe were $10^{10}$ molecules of the complex to $10^{11}$ copies of the probe.

10 uL of target DNA was made in increasing quantity from $10^3$ to $10^8$ copies per tube. To these samples, 10 uL of the BSA-bio-TAG-SA-C probe complex, 10 uL of the biotinylated A probe and 25 uL of 10 ug Dynal SA coated M280 paramagnetic beads along with 10 uL of 100 ug/mL yeast was added. This mixture was incubated for 25 min at room temperature with agitation. After this period, 200 uL of a phosphate buffer was added and the samples read on the IGEN ORIGEN Analyzer.

Figure 13:
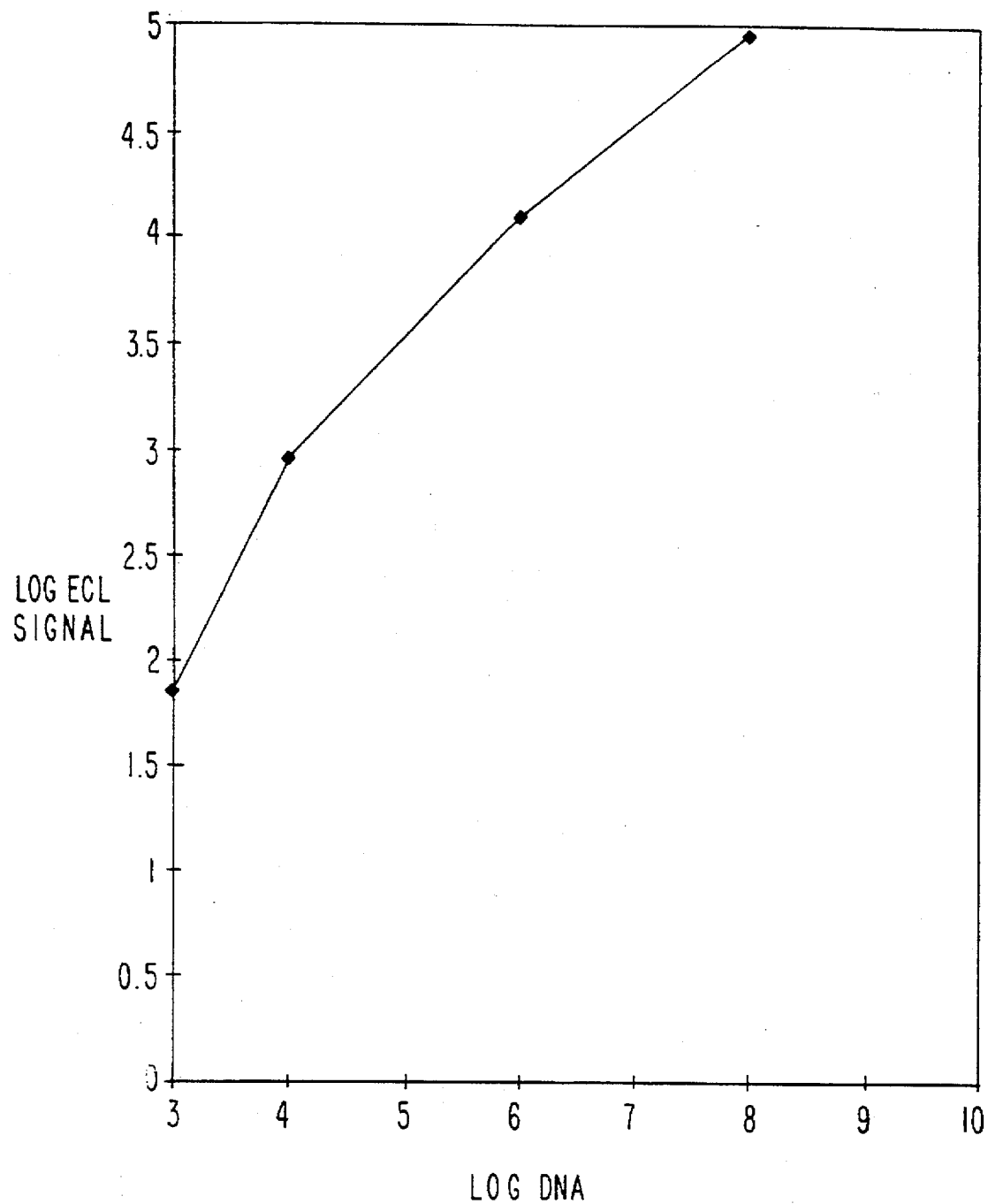

Cutoff value and significance of results were calculated as done previously. The data indicated a sensitivity of 1000 molecules of the target DNA with a range extending to $10^8$ molecules (highest sample tested). The slope of the plotted data indicated an increase in signal of three orders of magnitude for the five order of magnitude increase in analyte. See FIG. 13.

Although the examples illustrate various modifications of the present invention, other variations will suggest themselves to those skilled in the art in light of the above disclosure. It is to be understood, therefore, that changes may be made in the particular embodiments described above which are within the full intended scope of the inventions as defined in the appended claims.

---

What is claimed is:

1. A multi-labelled probe complex, comprising:
   (a) a biotinylated bovine serum albumin platform molecule;
   (b) a plurality of electrochemiluminescent labels attached to the platform molecule; and
   (c) a detection oligonucleotide probe attached to the platform molecule.

2. The labelled probe complex of claim 1, wherein, the oligonucleotide probe is attached to the platform molecule through a covalent bond or through a receptor-ligand interaction.

3. The labelled probe complex of claim 2 wherein the oligonucleotide probe is attached to the platform molecule through a receptor-ligand interaction.

4. The labelled probe complex of claim 3 wherein the receptor-ligand interaction is the binding of biotin to avidin.

5. The labelled probe complex of claim 4, wherein the probe is also biotinylated and the interaction comprises streptavidin interaction with both the biotin moiety of the platform molecule and the biotin moiety of the probe.

6. The labelled probe complex of claim 1, wherein the label is a derivative of Ru(bpy)$_3^{+2}$ which is attached to the biotinylated bovine serum albumin through a covalent bond.

7. The labelled probe complex of claim 6, wherein the covalent bond comprises an amide linkage.

8. The labelled probe complex of claim 1, wherein the biotinylated bovine serum albumin is capped with streptavidin.

9. The labelled oligonucleotide complex of claim 6 wherein:
   (a) the platform molecule is biotinylated bovine serum albumin wherein a plurality of biotin molecules are covalently bonded to the platform molecule; each biotin molecule being further noncovalently attached through corresponding receptor-ligand interactions with a corresponding avidin molecule, wherein the bonding and attaching of the biotin molecules does not interfere with the activity of any other portion of the complex;
   (b) each label is covalently bonded to the platform molecule; wherein the bonding of the labels does not interfere with the activity of any other portion of the complex;
   (c) the oligonucleotide probe is a biotinylated nucleotide sequence wherein a biotin molecule is covalently bonded thereto; the biotin molecule being further noncovalently attached through receptor-ligand interactions with a avidin molecule; wherein the bonding and attaching of the biotin molecules does not interfere with any other portion of the complex; and
   (d) wherein the complex is useful for performing assays for an analyte of interest having a target nucleotide sequence involving:

(1) the hybridization of at least a portion of the nucleotide sequence of the probe to at least a portion of the target nucleotide sequence;

(2) the generation of electrochemiluminescence upon the exposure of the complex to electrochemical energy; and (3) the detection of the generated electrochemiluminescence.

10. An electrochemiluminescent labelled complex comprising a biotinylated bovine serum albumin platform molecule covalently bonded to multiple electrochemiluminescent labels.

11. An electrochemiluminescent labelled complex according to claim 10 wherein the electrochemiluminescent label of the labelled complex is a derivative of $Ru(bpy)_3^{+2}$.

12. A labelled complex comprising:

(a) a biotinylated bovine serum albumin platform molecule wherein a plurality of biotin molecules are each covalently bonded to the platform molecule; each biotin molecule being further noncovalently attached through corresponding receptor-ligand interactions with a corresponding avidin molecule; wherein the bonding and attaching of the biotin molecules does not interfere with the activity of any other portion of the complex;

(b) a plurality of electrochemiluminescent labels each being a derivative of $Ru(bpy)_3^{+2}$ covalently bonded to the platform molecule; wherein the bonding of the labels does not interfere with the activity of any other portion of the complex; and (c) wherein the complex is useful for performing assays for an analyte of interest having a target nucleotide sequence involving:

(1) an oligonucleotide probe being a nucleotide sequence having a biotin molecule attached thereto and wherein the biotin molecule of the probe is capable of noncovalently attaching through receptor-ligand interactions with an avidin molecule;

(2) the hybridization of at least a portion of the nucleotide sequence of the probe to at least a portion of the target nucleotide sequence;

(3) the generation of electrochemiluminescence upon the exposure of the complex to electrochemical energy; and (4) the detection of the generated electrochemiluminescence.

13. A kit for carrying out a nucleic acid hybridization test to detect a target nucleotide sequence comprising, a biotinylated platform molecule carrying multiple electrochemiluminescent labels and an oligonucleotide probe which specifically hybridizer to a part of said sequence, magnetic beads comprising streptavidin, and a biotinylated oligonucleotide probe which specifically hybridizes to a different part of said sequence attached to said magnetic beads.

14. A method for carrying out a nucleic acid hybridization test to detect a target nucleotide sequence comprising, (a) contacting a sample suspected of containing the target nucleotide sequence with both a multi-labeled probe complex according to claim 1 wherein the oligonucleotide probe specifically hybridizes to a portion of the target nucleotide sequence and with streptavidin coated magnetic beads including another oligonucleotide probe which specifically hybridizes to a different portion of said sequence under hybridization conditions to form a hybridization product; and (b) subjecting the hybridized product of step (a) to conditions which result in electrochemiluminescence; and (c) measuring the resulting electrochemiluminescence.

15. The labelled probe complex of claim 1, wherein the oligonucleotide probe is attached to the platform molecule through a covalent bond.

16. The labelled probe complex of claim 3, wherein the receptor-ligand interaction is the binding of biotin to avidin.

17. The labelled probe complex of claim 1, wherein the biotinylated bovine serum albumin contains approximately eleven biotin moieties attached to each molecule of bovine serum albumin.

18. The labelled probe complex of claim 17, wherein the bovine serum albumin is capped with streptavidin through streptavidin-biotin interactions.

19. The labelled probe of claim 6, wherein about 10 to about 20 labels are attached to the platform molecule.

20. A multi-labelled probe complex, comprising:

(a) a biotinylated bovine serum albumin platform molecule;

(b) a plurality of $Ru(bpy)_3^{+2}$ derivative labels attached to the platform molecule through an amide linkage; and (c) a detection oligonucleotide probe attached to the platform molecule through a receptor-ligand interaction which is the binding of biotin to streptavidin.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 58 base pairs
( B ) TYPE: nucleic acid
( C ) STRANDEDNESS: single
( D ) TOPOLOGY: linear ( i i ) MOLECULE TYPE: OLIGONUCLEOTIDE ( x i ) SEQUENCE DESCRIPTION: SEQ ID NO:1:

GGTAGCTGAA TTTGTTACTT GGCTCATTGT CCCTGACATG CTGTCATCAT TTCTTCTA        5 8

( 2 ) INFORMATION FOR SEQ ID NO:2:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: OLIGONUCLEOTIDE ( x i ) SEQUENCE DESCRIPTION: SEQ ID NO:2:

TAGAAGAAAT GATGACAGCA TGTCAGGGA        2 9

( 2 ) INFORMATION FOR SEQ ID NO:3:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear (ii) MOLECULE TYPE: OLIGONUCLEOTIDE (xi) SEQUENCE DESCRIPTION: SEQ ID NO:3:

CAATGAGCCA AGTAACAAAT TCAGCTACC  29

(2) INFORMATION FOR SEQ ID NO:4:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: OLIGONUCLEOTIDE (xi) SEQUENCE DESCRIPTION: SEQ ID NO:4:

CGACTGTCAT CTATCTACAC TGTCTGCAGC TTCCTCATTG ATGGTCTCTT TTAACA  56

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: OLIGONUCLEOTIDE (xi) SEQUENCE DESCRIPTION: SEQ ID NO:5:

CATGCACTGG ATGCACTCTA TCCCATTCTG CAGCTTCTTC ATTGATGGTC TCTTTTAACA  60

(2) INFORMATION FOR SEQ ID NO:6:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: OLIGONUCLEOTIDE (xi) SEQUENCE DESCRIPTION: SEQ ID NO:6:

TGTTAAAAGA GACCATCAAT GAGGA  25

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: OLIGONUCLEOTIDE (xi) SEQUENCE DESCRIPTION: SEQ ID NO:7:

GAATGGGATA GAGTGCATCC AGTGCATG  28

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: OLIGONUCLEOTIDE (xi) SEQUENCE DESCRIPTION: SEQ ID NO:8:

GACAGTGTAG ATAGATGACA GTCG                                              24

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: OLIGONUCLEOTIDE ( x i ) SEQUENCE DESCRIPTION: SEQ ID NO:9:

TGTTAAAAGA GACCATCAAT GAGGA                                              25

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: OLIGONUCLEOTIDE ( x i ) SEQUENCE DESCRIPTION: SEQ ID NO:10:

GAATGGGATA GAGTGCATCC AGTGCATG                                           28

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: OLIGONUCLEOTIDE ( x i ) SEQUENCE DESCRIPTION: SEQ ID NO:11:

GACAGTGTAG ATAGATGACA GTCG                                               24